United States Patent [19]
Jensen

[11] Patent Number: 5,632,618
[45] Date of Patent: May 27, 1997

[54] APPARATUS FOR THE TREATMENT OF OVERBITE

[76] Inventor: Erling R. Jensen, Ibsgaarden 35, Himmelev, DK-4000 Roskilde, Denmark

[21] Appl. No.: 545,786
[22] PCT Filed: May 6, 1994
[86] PCT No.: PCT/DK94/00183
§ 371 Date: Nov. 13, 1995
§ 102(e) Date: Nov. 13, 1995
[87] PCT Pub. No.: WO94/26198
PCT Pub. Date: Nov. 24, 1994

[30] Foreign Application Priority Data

May 10, 1993 [DK] Denmark ................. 0543/93
Mar. 1, 1994 [DK] Denmark ................. 0241/94

[51] Int. Cl.$^6$ .................................................. A61C 3/00
[52] U.S. Cl. ................................................... 433/19
[58] Field of Search .......................... 433/18, 19, 21

[56] References Cited

U.S. PATENT DOCUMENTS 4,462,800  7/1984  Jones ................................ 433/19
4,795,342  1/1989  Jones ................................ 433/19

FOREIGN PATENT DOCUMENTS

WO-A1-9011731  10/1990  WIPO.
WO-A1-9219174  11/1992  WIPO.

*Primary Examiner*—Cary E. O'Connor
*Attorney, Agent, or Firm*—Leydig, Voit & Mayer, Ltd.

[57] ABSTRACT

The invention relates to an apparatus for the treatment of overbite, said apparatus comprising a first band (12) on the front premolars in the lower jaw and a second band (13) on the front molars in the upper jaw, said bands (12, 13) being connected by a rod (14) consisting of an insertion part (15) which may telescopically slide into a receiving part (16). In order to assemble or disassemble the apparatus the end of the insertion part (15) facing the first band (12) is inserted pivotably into the side face of a first bushing (25) and the receiving part (16) is provided with a tube (19) designed to receive a rod (17) on the insertion part, said tube (19) having an arm (20, 22) which is inserted pivotably into the side face of a second bushing (25, 25a, 25b), and at least one of the two bushings (25, 25a, 25b) is via a pin (34) secured to its band (12, 13) by a laterally of the bushing (25) insertable or removable, respectively, locking ring or a similar device (33).

There is thus achieved a safe and secure connection between the telescopic rods (14) and the bands (12, 13) without any use of screws which might loosen during the use and then be swallowed by the user.

There is also described a method for assembling respectively disassembling the apparatus.

13 Claims, 9 Drawing Sheets

APPARATUS FOR THE TREATMENT OF OVERBITE

The invention relates to an apparatus for the treatment of overbite, said apparatus comprising at either side of a user's mouth a first band on the front premolars in the lower jaw and a second band on the front molars in the upper jaw, said first and second bands being connected by a rod consisting of an insertion part which may telescopically slide into a receiving part, whereby said insertion part and said receiving part are pivotably mounted on said first and second band, respectively, and said receiving part being provided with a tube designed to receive a rod on the insertion part.

The invention also relates to a method for assembling the apparatus.

Many people suffer from overbite meaning that the lower jaw is short relative to the upper jaw so that when biting the incisors of the lower jaw cannot meet the incisors of the upper jaw in the correct manner with the sharp edges of the incisors against each other in an edge to edge position. Instead the sharp edges of the incisors of the lower jaw will rest a longer or shorter distance to the rear in the user's mouth relative to the corresponding edges of the incisors of the upper part of the mouth.

In order to remedy this disorder there may be used various forms of apparatuses or devices which can exert pressure between the lower and the upper jaws so that the lower jaw is forced forwards relative to the upper jaw. When exerted to such pressure, the lower jaw is made to grow in such a direction that the overbite will be reduced and finally be fully adjusted. This applies not only to children and young people, but also to mature people.

An apparatus of this kind is a socalled Herbst apparatus, which is a fixed apparatus comprising telescopic rods extending from the front molars of the upper jaw to the front premolars of the lower jaw. At the beginning of the treatment the telescopic rods are designed to have such a length that the lower jaw will be pressed forwards to take an edge to edge position.

The rods are telescopically designed so that they will extend when the mouth is opened, whereas when the mouth is closed they are fully nested within each other to be capable of exerting the required displacement pressure on the lower jaw. The individual parts of the telescopic rods are of course proportioned so that they cannot come apart when the mouth is fully opened.

During the active treatment period of 6–10 months it is necessary to change the telescopic rods so that the lengths thereof in the fully nested position are extended stepwise to compensate for the gradual extension of the lower jaw, when this grows forward as intended by the treatment.

The telescopic rods must therefore be removable to permit a replacement of same without an extremely difficult dismounting of the bands on the teeth.

By the known apparatus the ends of the telescopic rods are therefore secured at either side of the user's mouth by means of screws to the bands around the respective teeth.

By unscrewing the screws a first set of telescopic rods may be replaced by a second set of telescopic rods which in their fully nested position are longer than the first set.

This structure is disadvantageous in that the screws, when in use, may loosen and finally fall off the respective bands around the teeth making the apparatus inoperative while at the same time risking that the user will swallow a stray screw or be hurt by the free end of the respective telescopic rod hitting the palate or other inner faces within the mouth when the mouth is closed. From WO 90/11731 an apparatus as initially described is known where each end of the telescopic rod is pivotably hold on a shaft and secured on said shaft by an arch wire which is inserted in an opening next to the free end of said shaft.

According to WO 92/19174 the free ends of the telescopic rod comprise ball cups receiving corresponding ball heads in a snap fit relation, said ball heads being mounted on molar bands.

Instead of replacing the set of telescopic rods, it has been tried to squeeze together small metal strips around the insertion part for forming a short ring or bushing between the receiving part and the attachment of the insertion part to the band around the front premolars in the lower part of the mouth thereby achieving an extension of the telescopic rods in their collapsed position. However, this apparently captivating solution has proved disadvantageous since due to their slits these rings or bushings will often be deformed in such a manner that they open and fall off the insertion part making the apparatus inoperative or such that the rings or bushings may be swallowed by the user.

It is the object of the invention to provide such an arrangement of the apparatus described in the introduction that the mentioned drawbacks may be overcome and that the telescopic rods may be replaced in a simple and easy manner without risking that joints between the telescopic rods and the bands around the teeth respectively that rings or bushings may loosen inadvertently when using the apparatus.

This object is achieved by an apparatus of the kind described in the introduction which apparatus according to the invention is characterised in that the end of the insertion part facing one of the bands is inserted pivotably in the side face of a first bushing, that is inserted pivotably in the side face of a second bushing, and that at least one of the two bushings via a pin is secured to its band by a laterally of the bushing insertable or removable locking ring or a similar device.

By removing the locking ring or the similar device through the side of at least one of the bushings, for example through the side of the first bushing, the connection between the insertion part and the first band will be removed, whereafter the insertion part may be pulled out of the receiving part. If both bushings are secured to its respective band by a locking ring or a similar device, the receiving part may in the same manner be removed from the second band, whereafter the telescopic rods may be replaced by a set the length of which in its telescoped position is longer that the length of the first used set. If, however, only one of the bushings is secured to its band with a locking ring or a similar device, it is one of the bushes, for example the first Bushing, which is secured to the first band with the locking ring or the similar device, whereas the second bushing for the receiving part is then screwed into the second band by means of a thread within the bushing.

It is also possible to utilise the same set of telescopic rods in that after the removal of the locking ring by the insertion part, it is possible to mount closed rings or bushings on the insertion part, whereby the set of telescopic rods will achieve a greater length in their fully nested position than originally. By this solution there is no risk that the rings or the bushings will open inadvertently since they are closed or without any form of slits.

After replacement of the telescopic rods or after mounting of rings or bushings on the insertion part only, the telescopic rods are remounted by proceeding in reverse order of the dismounting order.

As mentioned in the introduction, the invention also relates to a method for assembling the apparatus, said method according to the invention being characterised by the following steps:

a) that the pin is mounted on one of the bands, b) that a locking ring or a similar device is extended in a diametrical direction and is slid around the stepping until the locking ring or the similar device on the arrival at the cut contracts and slides into the cut, c) that the ball of the insertion part is inserted into the female bore of the bushing with the rod projecting through the slit, d) that the bushing is arranged on the pin, e) that pressure is exerted in axial direction towards the pin when the chamfer Of the bushing rests on the locking ring so that the inclined chamfer presses the locking ring or the similar device diametrically together, f) that the bushing is slid to the bottom of the pin so that the locking ring or the similar device may expand to its normal diameter and mesh with the cut in the inner wall when the locking ring is on level with the cut, g) that the tube of the receiving part is mounted on the rod, h) and that the above steps a) to f) are repeated so as to mount the receiving part on the opposite band.

The dependent claims relate to advantageous embodiments of the apparatus according to the invention in that the expediency of these embodiments will appear from the following.

The apparatus and the method according to the invention will be further explained by means of preferred embodiments in the following detailed part of the specification with reference to the drawing wherein.

Figure 1:
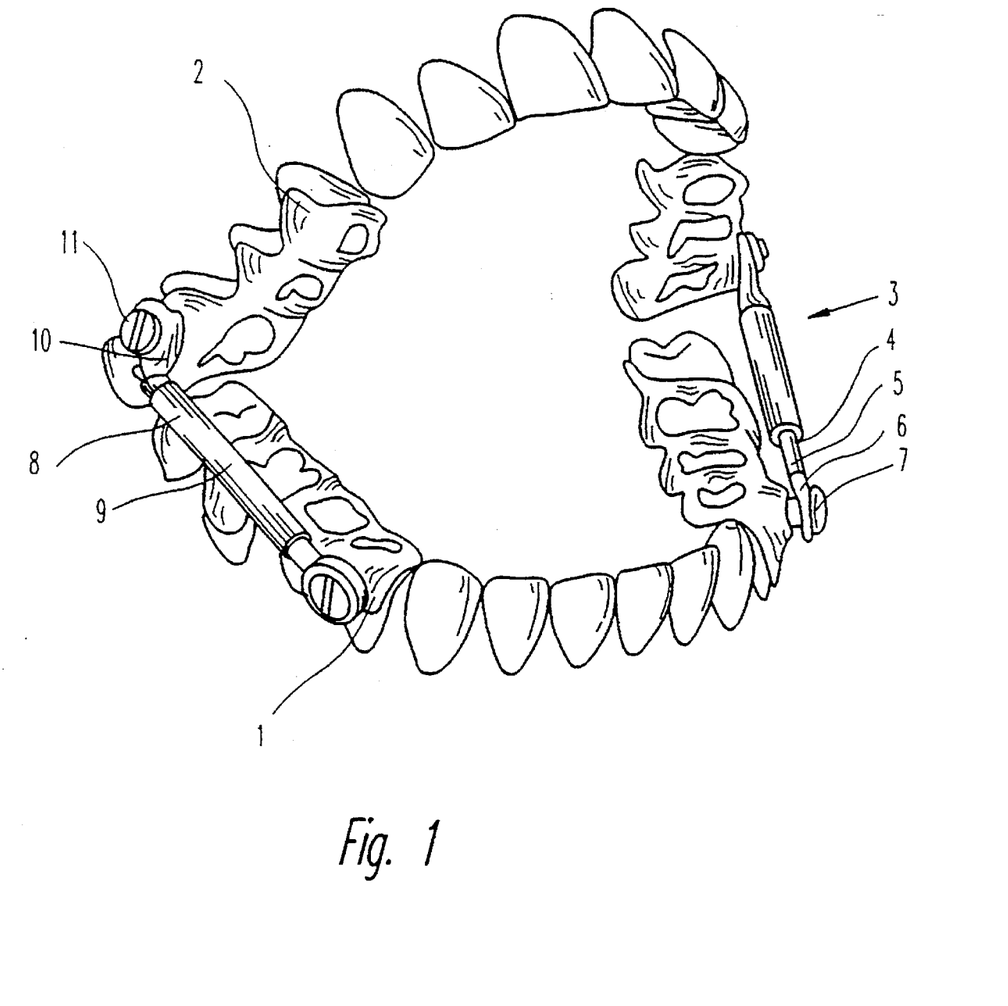
FIG. 1 is a perspective view of a known apparatus for the treatment of overbite arranged on a model of a denture.

The known apparatus shown in FIG. 1 is mounted on a denture model with an upper and lower mouth part, and the apparatus comprises at either side a first band 1 arranged on the front premolars of the lower mouth part and a second band 2 arranged around the front molars of the upper mouth part. Such bands 1,2 are generally available for use in dental treatment. Between the first and the second band there is at either side provided a telescopic rod 3.

Each telescopic rod 3 extends between the front end of the first band 1 and the rear end of the second band 2 and consists of an insertion part 4 and a receiving part 8.

The bands 1,2 and the telescopic rods 3 in the two sides of the apparatus are symmetrical about a plane dividing the upper and lower jaw along their centre.

The insertion part 4 comprises a straight rod 5 of a cylindrical cross-section, said rod 5 having at the front end in the position of use a flat elongation 6 with a hole for receiving a screw 7 which by screwing into a bore with a female thread in the first band 1 may retain the insertion part 4 in a pivotable manner onto the first band 1.

The receiving part 8 comprises a straight tube 9 which can slideably receive the rod 5 in the longitudinal direction thereof. At the rear end in the position of use of the tube 9, this is provided with a flat elongation 10 with a hole for receiving a screw 11 which can retain the receiving part 8 onto the second band 2 at the rear end thereof, which has a bore with a female thread. The elongation 10 is offset sidewise relative to the longitudinal axis of the tube 9 so that after mounting within the tube 9 the rod 5 with its free end may without hindrance pass the elongation 10.

The holes for the screws 7 and 11 have a somewhat larger diameter than the diameter of the shafts of the screws so as to achieve a certain mobility in the connections whereby the lower mouth part is movable slightly sidewise relative to the upper mouth part.

When the mouth is opened as shown in FIG. 1, the rod 5 of the insertion part 4 will be drawn somewhat out of the tube 9 of the receiving part 8, and when the mouth is closed, the mutual lengths of the insertion part 4 and the receiving part 8 will be adapted such that the telescopic rods 3 in their fully compressed state will press the lower jaw forwards.

As long as the telescopic rods 3 are so long that they can force the lower jaw forwards towards an edge to edge position of the incisors, the lower jaw will grow forwards so that the overbite is gradually reduced. Having used the apparatus for some time, the lower jaw will have grown to such an extent that the telescopic rods can no longer press the lower jaw forwards. In order to completely remove a big overbite it is therefore necessary to replace the set of telescopic rods 3 by another set, the length of which in its compressed position is longer that the corresponding length of the first set.

For this purpose the screws 7, 11 are removed and the telescopic rods 3 replaced.

When using the apparatus there is a risk that the screws 7, 11 will work their way out of the bores in the first 1 and the second band 2 whereafter the user may perhaps swallow the screws.

Figure 2:
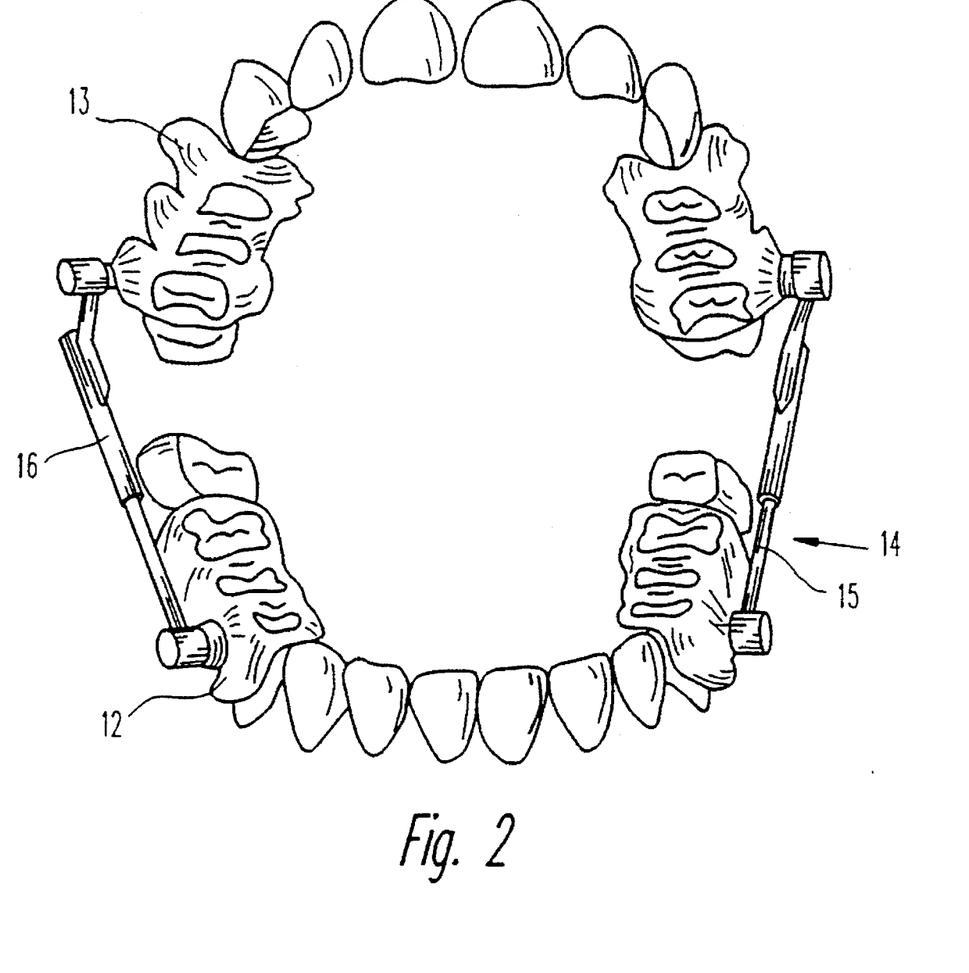
FIG. 2 is a perspective view of an apparatus according to the invention which is likewise arranged on a model of a denture.

This drawback is overcome by the apparatus according to the invention shown in FIG. 2 wherein the telescopic rods are designed and secured in a different manner.

The apparatus in FIG. 2 has a first band 12, a second band 13 and telescopic rods 14 connecting the first band with the second band, and the telescopic rods 14 comprise an insertion part 15 and a receiving part 16.

Figure 3:
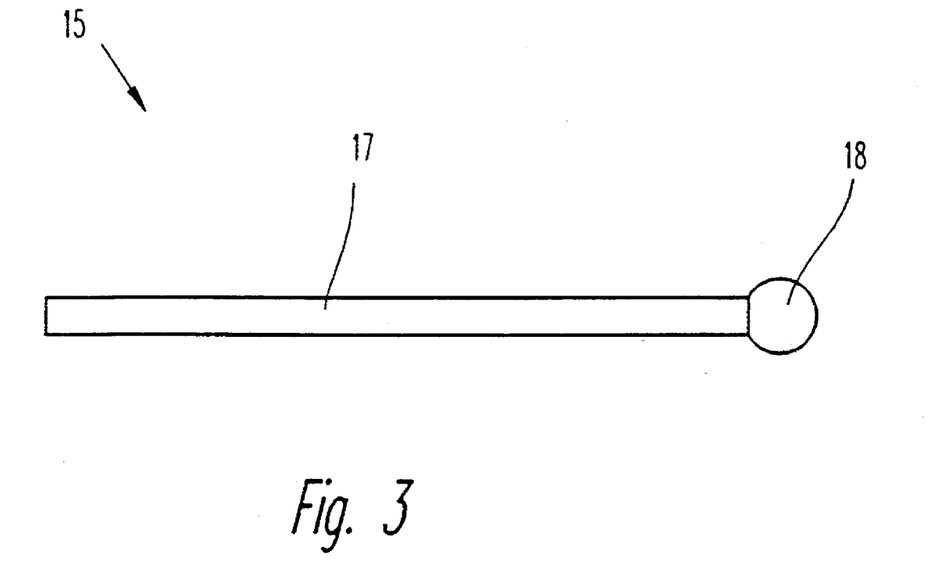
FIG. 3 is an insertion part for the apparatus in FIG. 2.

The insertion part 15 comprises, as shown in FIG. 3, a straight rod 17 of a circular cross-section and a ball 18 at one end thereof, said ball having a diameter which is slightly greater than that of the rod 17.

Figure 4:
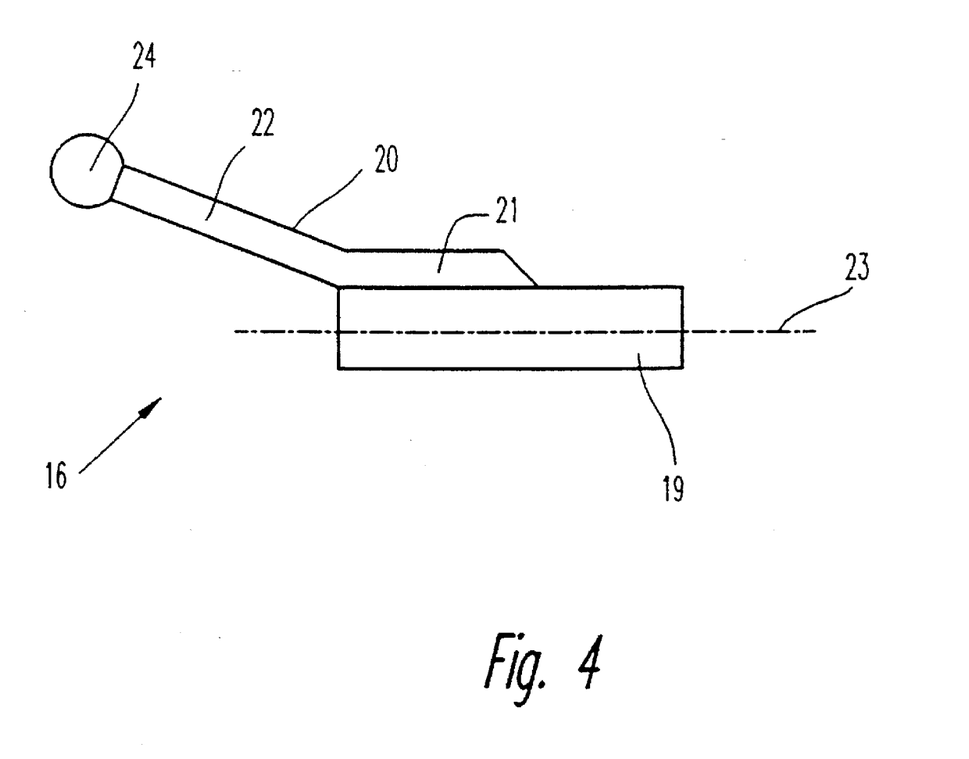
FIG. 4 is a side view of a first embodiment of a receiving part for the apparatus in FIG. 2.

As shown in FIG. 4, the receiving part 16 comprises a tube 19 for slideably receiving the rod 17. At the side of the tube 19 and at one end thereof there is secured an arm 20. The arm 20 is bent such that a first part 21 of the arm extends along and is secured to the tube 19, whereas the other part 22 of the arm extends past the end of the tube 19 and at an angle relative to the longitudinal axis 23 of the tube 19. There is secured a ball 24 at the free end of the other part 22 of the arm 20. The arm 20 and the ball 24 have the same diameter as the rod 17 and the ball 18, respectively, on the insertion part 15.

Figure 4A:
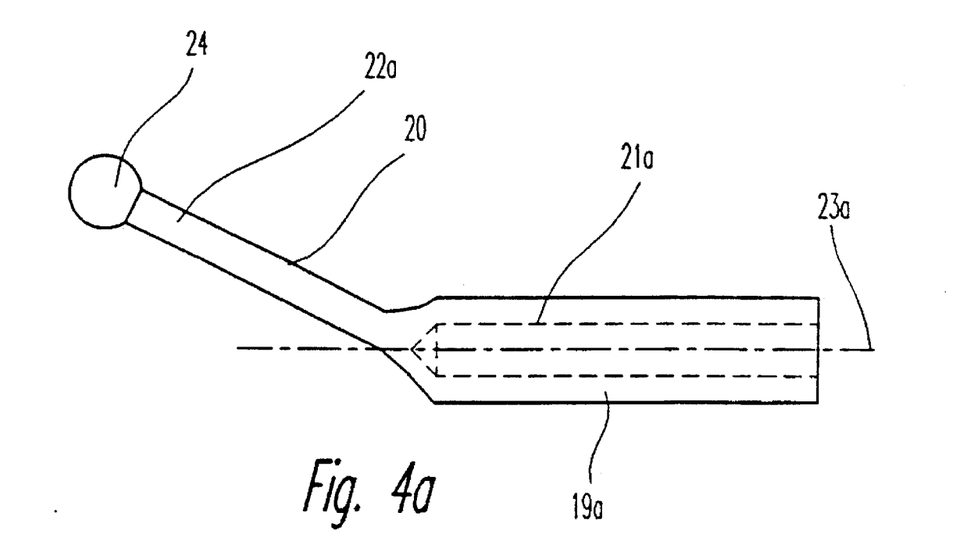
FIG. 4a is a side view of a second embodiment of a receiving part.

FIG. 4a illustrates another embodiment of the receiving part 16. Here the first part 21 has a longitudinal bore to the effect that the first part 21a can receive the rod 17 of the insertion part 15 in the bore. The connection between the first part 21 shown in FIG. 4 and the tube 19 is hereby avoided.

Figure 5:
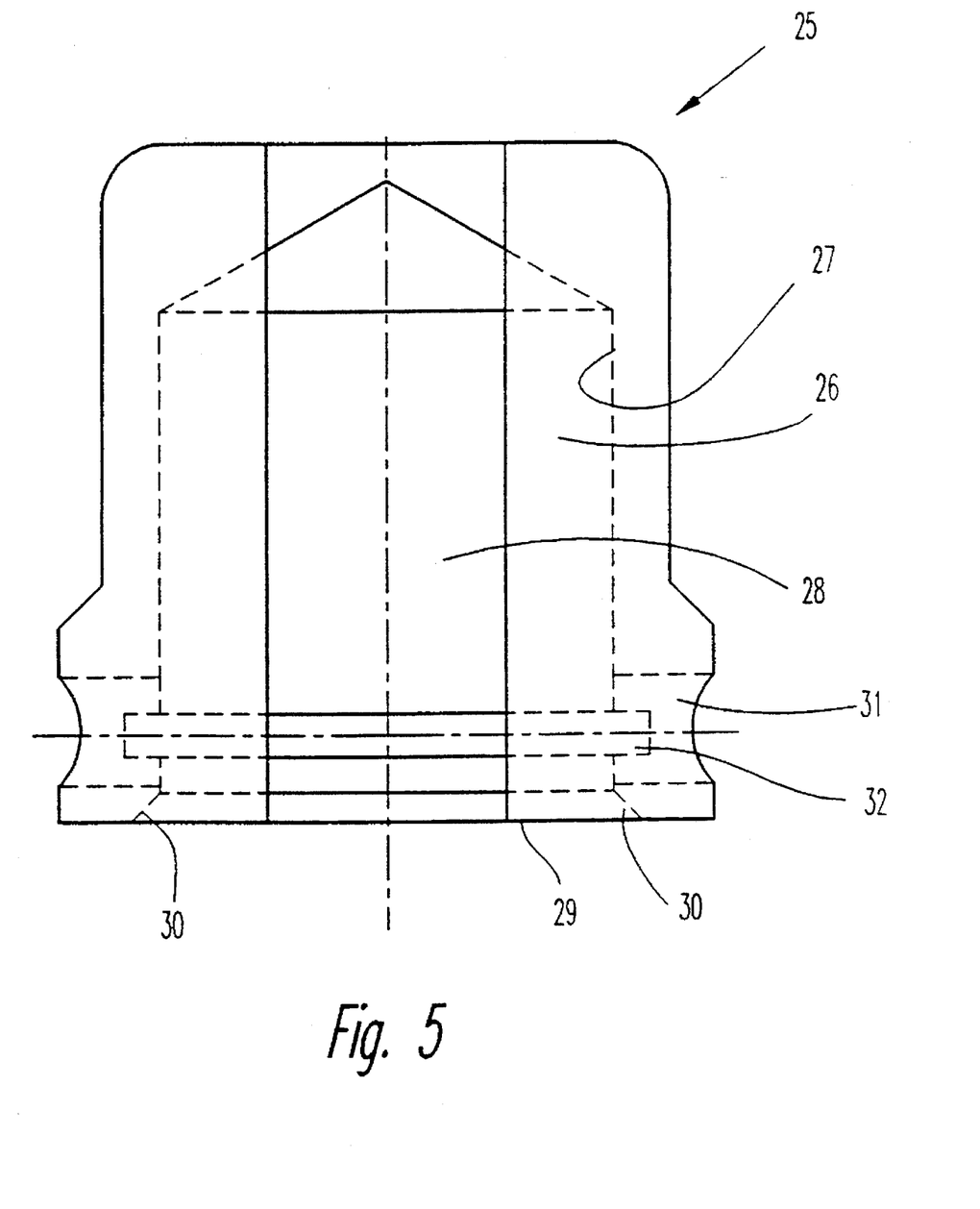
FIG. 5 is a side view of a bushing for receiving either a ball on the insertion part shown in FIG. 3 or a ball on the receiving part shown in FIG. 4.

The balls 18 and 24 are mounted in each its cup-shaped bushing 25, which is shown in FIG. 5. The bushing 25 has a bottom hole or a bore 26 with an inner wall 27 and an elongate slit 28 extending along the axial direction of the bushing and extend from the bottom of the bore 26 and at least some distance towards the free end 29 of the bushing. When the slit 28 does not extend all the way towards the free end 29 of the bushing, the slit 28 may possibly extend along both diametrically opposite sides of the bushing. The width of the slit 28 is only somewhat larger than the diameter of the rod 17 and the other part 22 of the arm 20. When the balls 18 and 24 are mounted in their respective bushings 25, the rod 17 of the insertion part 15 and the tube 19 of the receiving part 16 will only be capable of pivoting a limited angle in a plane determined by the longitudinal axis of the bushing 25 and through the centre of the slit 28 and cannot swing out of this plane, see FIG. 8.

The passage between the bore 26 and the free end 29 is provided with a chamfer 30.

Figure 6:
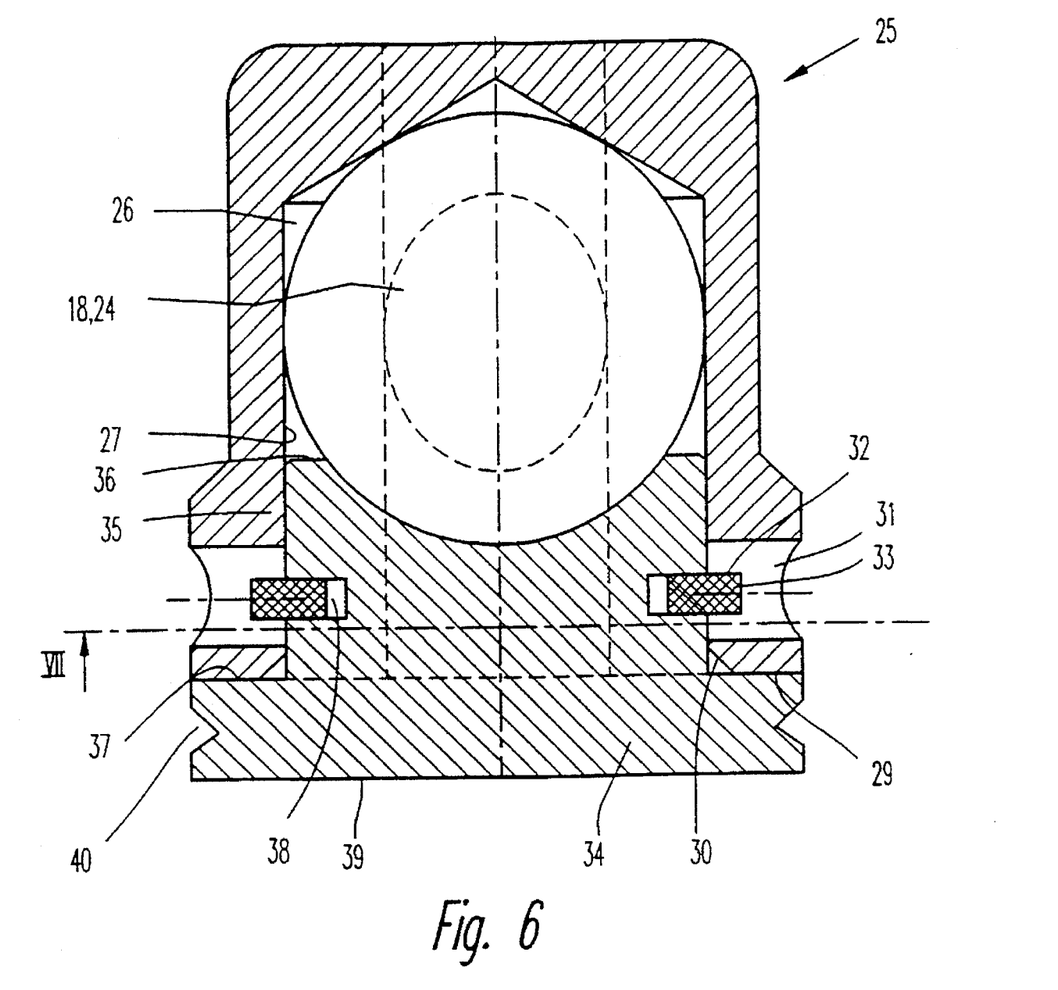
FIG. 6 is an axial section of the bushing in FIG. 5 in that the bushing has been mounted on a pin after reception of a ball.
Figure 7:
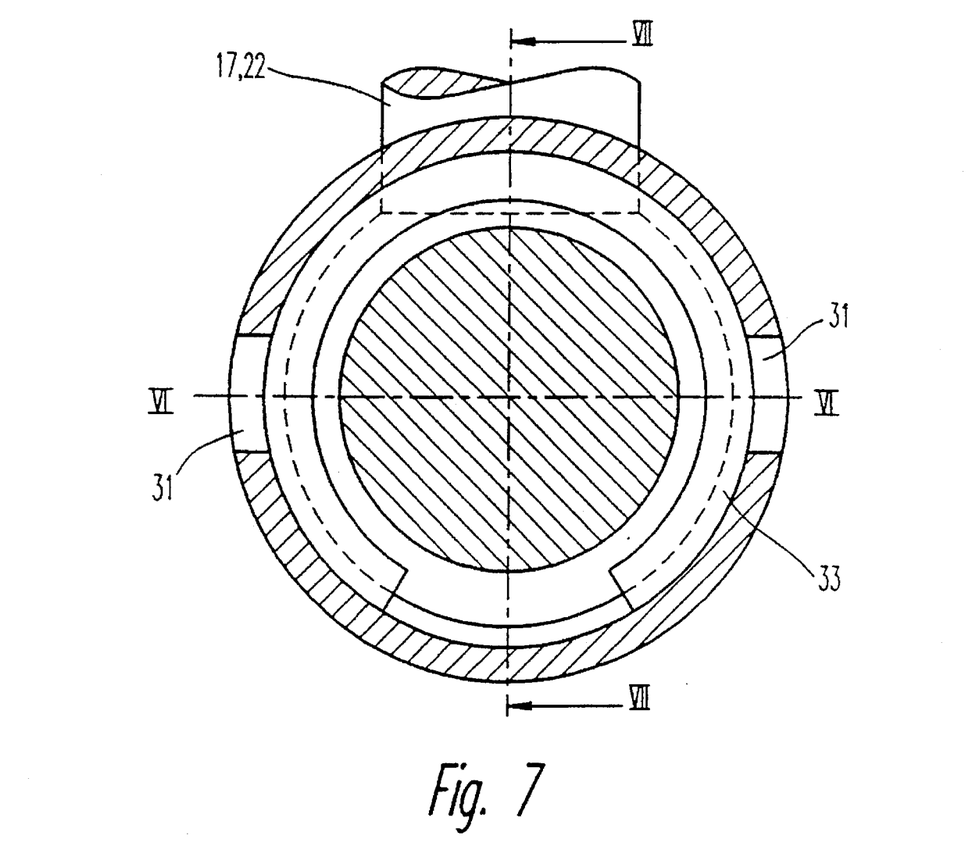
FIG. 7 is the section in the bushing shown by the line VII—VII in FIG. 6.
Figure 8:
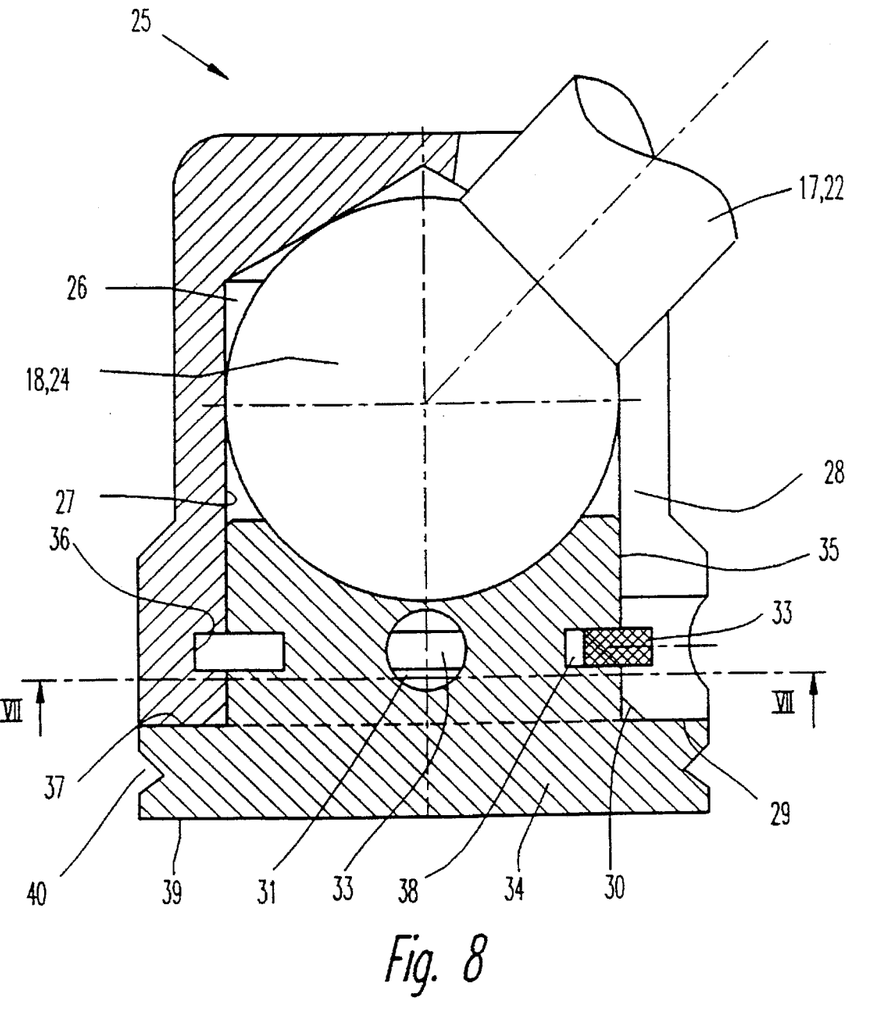
FIG. 8 is the section in the bushing shown by the line VIII—VIII in FIG. 7.

Close to the free end 29 of the bushing 25 there is a diametrical throughbore 31. On level with the bore 31 there is a peripherally extending cut or groove 32 in the inner wall 27 for receiving a locking ring 33, as shown in FIGS. 6, 7 and 8.

By means of the locking ring 33 there is provided a releaseable connection between a bushing 25 and a pin 34. The pin 34 has a circular cross-section and has an external stepping 35 extending from the first end 36 of the pin with a diameter corresponding to the diameter of the bore 26 of the bushing 25 in that the end face 37 of the stepping forms a rest for the free end 29 of the bushing 25 when same is mounted on the pin. On the stepping 35 there is a peripherally extending cut or groove 38 for receiving the locking ring 33. The cut 38 has such a depth that the locking ring 33, which can be pressed together diametrically, may be accomodated in its compressed state in the cut 38 without projecting beyond the stepping 35. The opposite other end 39 of the pin is intended for casting with a first band 12 or a second band 13 depending on whether the bushing 25 and the pin 34 are to be used for mounting an insertion part 15 and a receiving part 16, respectively.

In order to achieve secure attachment of the pin 34 to a band 12, 13, there is an external circumferential groove 40 so that the casting material used by the casting of the band 12, 13 may fill into the groove 40. If so preferred, the pin 34 may also by soldered or welded to a commercially available band.

When assembling the apparatus according to the invention, there is proceeded in the below mentioned manner in that the mounting of the insertion part 15 on one of the bands 12 or 13 is first described, and it will be understood that the mounting of the receiving part 16 on the opposite band 13 respectively 12 will be quite analogous thereto.

The pin 34 is mounted on the band 12, 13 in question whereafter the locking ring 33 is extended in a diametrical direction and slid over the stepping 35 until the locking ring 33, on the arrival at the cut 38, contracts due to its elasticity.

The ball 18 of the insertion part 15 is inserted into the female bore 26 of the bushing 25 with the rod 17 projecting through the slit 28. The bushing 25 is then arranged on the pin 34. When the chamfer 30 of the bushing rests on the locking ring 33, pressure is exerted in axial direction towards the pin 34 whereby the inclined chamfer 30 will press the locking ring diametrically together so that the bushing 25 can now by slid to the bottom of the pin 34. This being done, the locking ring 33 will be situated on level with the cut 32 in the inner wall 27 whereafter the locking ring will expand to take its normal diameter and mesh with the cut.

The locking ring 33 now fills out the cut 32 as well as the cut 38 whereby the bushing 25 and the pin 34 are locked together, and the ball 18 is at the same time prevented from falling out of the slit 28.

After the mounting of the insertion part 15 the receiving part 16 can be mounted in the same manner in that the rod 17 of the insertion part will first have to be slid into the tube 19 of the receiving part 16 before the bushing 25 of the receiving part is pressed in place on its pin 34. When disassembling the apparatus according to the invention there is initially used a not shown tool, such as a pair of tongs or a similar tool with two jaws which can be pressed together.

With this tool the locking ring 32 is pressed diametrically together in that the two jaws of the tool are inserted into the diametric bore 31 in the bushing 25 and act on and press together the locking ring so that the locking ring 33 is now fully situated within the cut 38 in the pin 34. It is now possible to draw away the bushing from the pin 34 in that the tool is still held tightly on the locking ring until the edge of the locking ring 33, which is closest to the free end 29, is caught by the inner wall 27 in the bushing so that the locking ring is retained in the compressed position by this wall without use of the tool until the bushing is totally free of the pin.

Figure 9:
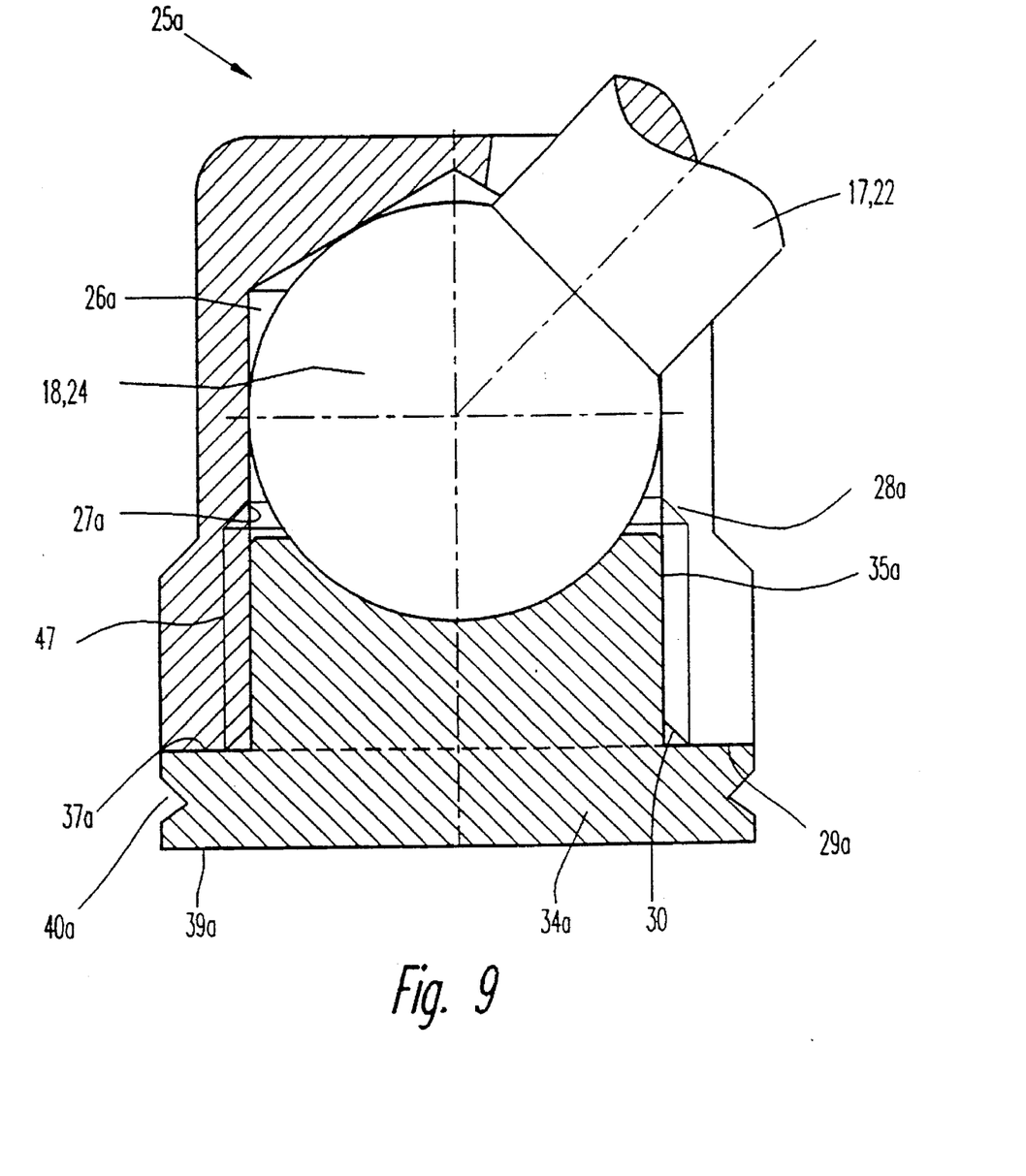
FIG. 9 is an axial section corresponding to FIG. 8 through another embodiment of a bushing in that the bushing is mounted on a pin after reception of a ball.

In another embodiment of the apparatus according to the invention it is also conceivable that only one of the bushings 25 is secured to its band by means of a locking ring 33. In that case it may be the first bushing 25 which is secured to the first band 12 by means of a removable locking ring 33, whereas the second bushing 25a is instead secured to the second band 13 by means of a threaded joint.

The second bushing 25a is then provided with a female thread 47 which replaces the peripheral cut or groove 32, whereas the bore 26a, the inner wall 27a and the slit 28a correspond to the equal parts 26, 27 and 28 in the first embodiment of the first bushing 25. The pin 34a for cooperation with the female thread 47 is likewise provided with a male thread on the stepping 35a of the pin 34a instead of the peripheral cut or groove 38.

When disassembling the apparatus according to this embodiment the locking ring 33 is removed from the first bushing 25 belonging to the insertion part 15 whereafter the rod 17 is slid out of the tube 19 of the receiving part 16.

The tube 19 is then placed in a position wherein the axis 23 of the tube 19 points to the side away from the user's upper jaw. It is now possible by means of the tube 19 and the arm 22 to rotate the second bushing 25a relative to the pin 34a in that during this rotation the tube 19 like a generatrix will describe a cylinder with a circular cross-section, whereas the arm 22 like a generatrix will describe a cone with its vertex in the ball 24. During the rotation the axis of this cylinder and cone may incline relative to the axis of the pin 34a and of the second bushing 25a since the ball 24 and the arm 22 provide the required flexibility relative to the bushing 25a.

When assembling the apparatus the procedure is reversed.

It will be obvious to a person skilled in the art that this second embodiment may also be accomplished when the pin 34a has a male thread and the second bushing 25a has a female thread.

Figure 10:
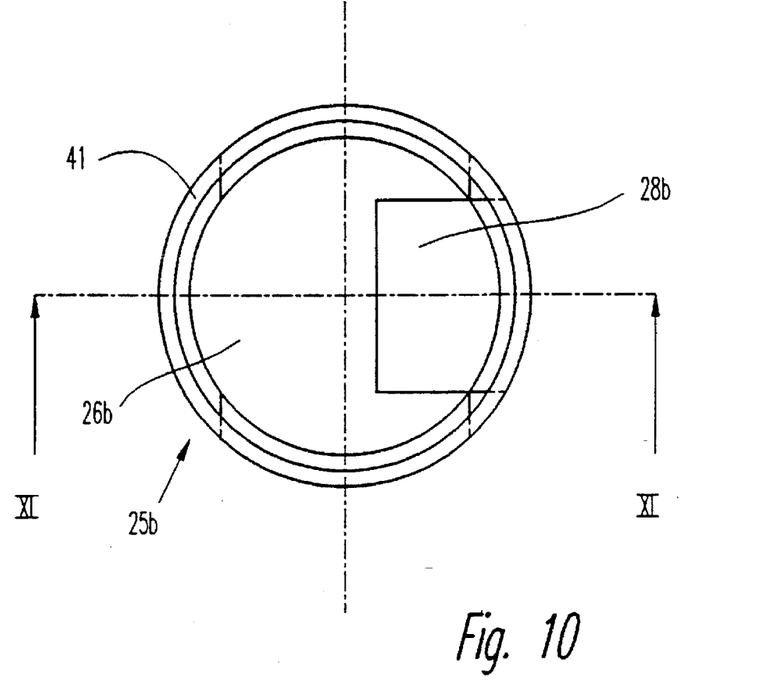
FIG. 10 is a view seen from the open end of a third embodiment of a bushing.
Figure 11:
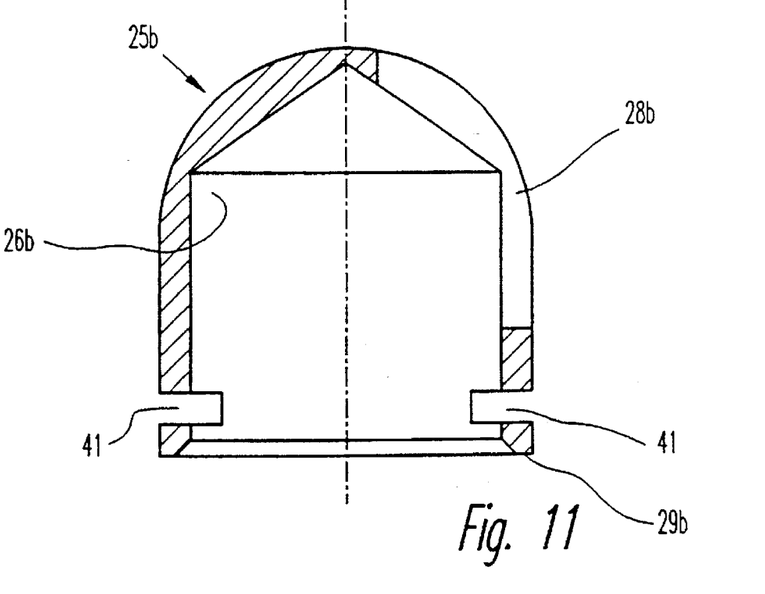
FIG. 11 is the section in the bushing shown by XI—XI in FIG. 10.

By a third embodiment of the apparatus according to the invention at least one of the bushings 25b may be provided with two slits 41 arranged on diametrically opposed sides of the bushing. The two slits 41 are arranged at such a distance of the end 29b of the bushing 25b that the slits 41 will precisely be situated on level with the cut 38 in a pin 34 when the pin is introduced into the bore 26b in the bushing. The slits 41 have furthermore one and the same depth and the diametric distance between the bottom of the slits corresponds to the diameter of the cut 38 in the pin 34. A locking ring or a similar device 33 may be slid over the bushing 25b when this is mounted on the pin 34 whereafter the locking ring or the similar device 33 may slide into the slits 41 as well as into the cut 38 such that the bushing 25b is locked onto the pin 34.

The locking ring or the similar device preferably consists of stainless steel or stainless wire. In a simple form of locking ring this may simply consist of a rubber band 33 which may mesh into the slits 41 and the cut 38.

By this embodiment both bushings may advantageously be secured in the described manner whereby it will be extremely easy to mount respectively dismount the apparatus according to the invention.

In the above description the coupling between the bushings 25, 25a, 25b, and the pins 34, 34a is illustrated in embodiments, wherein is used a locking ring 33 or a similar device. A locking ring or a similar device may be rustproof springwire, rustproof steel wire or elastomer, for example an elastic. It will be obvious for a person skilled in the art that any element capable of connecting in a form-locking manner a bushing of the described type with a pin will be suitable for the purpose.

I claim:

1. An apparatus for correcting an overbite in a patient having front premolars in both their upper and lower jaws, the apparatus comprising:

first and second bands, one of the bands securing the apparatus to the front premolars in the patient's lower jaw and the other band securing the apparatus to the front premolars in the patient's upper jaw;

a telescopic component coupled between the first and second bands, the telescopic component including (1) a receiving part having a tube and an arm, and (2) an insertion part including a rod having a first end and a second end, the first end of the rod of the insertion part being slidably disposed in the tube of the receiving part; and, first and second bushings for pivotably coupling the telescopic component to the first and second bands, each of the bushings defining a bore and including a slot in communication with the bore, each slot being disposed in a side of its respective bushing, the second end of the rod being pivotably secured in the first bushing with the rod extending through the slot of the first bushing, a first end of the arm associated with the receiving part being pivotably secured in the second bushing with the arm extending through the slot of the second bushing, at least one of the bushings being removably secured to its respective band by a pin and a locking ring.

2. An apparatus as defined in claim 1, wherein the locking ring comprises a stainless steel ring.

3. An apparatus as defined in claim 1, wherein each bushing is secured to its respective band by a pin and a locking ring.

4. An apparatus as defined in claim 3, wherein the first and second bushings are cup-shaped each of the first and second bushings has an axial bottom hole in communication with its bore, the bores of the first and second bushings are each defined by an inner wall, each inner wall includes a bushing groove, and each of the pins includes a pin groove positioned for communication with one of the bushing grooves defined in the inner wall of one of the bushings when the pins are inserted into the bores of their respective bushings such that one of the locking rings can be simultaneously disposed in the pin groove and the bushing groove of each cooperating pin and bushing.

5. An apparatus as defined in claim 1, wherein at least one of the first and second bushings is cup-shaped and includes an axial bottom hole in communication with its bore, the bore of the at least one bushing includes a female thread, and the pin cooperating with the bore of the at least one bushing includes a male thread on its periphery for mating with the female thread of the at least one bushing.

6. An apparatus as defined in claim 1, wherein at least one of the first and second bushings is cup-shaped and is provided with an axial bottom hole, the at least one bushing includes parallel slits disposed at diametrically opposite sides of the at least one bushing, the pin which cooperates with the bore of the at least one bushing has a wall including a pin groove positioned for communication with the slits of the at least one bushing when the pin is inserted into the bore, and the slits have a depth such that the locking ring can be simultaneously disposed in the parallel slits of the at least one bushing and in the pin groove.

7. An apparatus as defined in claim 1, wherein the second end of the rod of the insertion part includes a ball disposed in the bore of the first bushing adjacent the pin such that the rod is rotatable about its longitudinal axis and can swing in a plane determined by the longitudinal axis and the slot of the first bushing.

8. An apparatus as defined in claim 1, wherein the tube of the receiving part has a longitudinal axis, and the arm of the receiving part includes: (1) a first part secured to the side of the tube in a plane substantially parallel to the longitudinal axis of the tube, and (2) a second part disposed at an angle to the longitudinal axis of the tube such that the tube is offset relative to the second bushing.

9. An apparatus as defined in claim 1, wherein the arm of the receiving part includes (1) a first part having a longitudinal axis and a longitudinal concentric bore disposed in substantial alignment with the longitudinal axis, (2) a second part disposed at an angle to the longitudinal axis of the tube such that the tube is offset relative to the second bushing.

10. An apparatus as defined in claim 1, wherein the locking ring comprises a rubber band.

11. An apparatus as defined in claim 1, wherein the first end of the arm of the receiving part includes a ball disposed in the bore of the second bushing adjacent the pin such that the arm is rotatable about its longitudinal axis and can swing in a plane determined by the longitudinal axis and the slot of the second bushing.

12. An apparatus as defined in claim 1 further comprising:

third and fourth bands, one of the bands securing the apparatus to the front premolars in the patient's lower jaw and the other band securing the apparatus to the front premolars in the patient's upper jaw;

a second telescopic component coupled between the third and fourth bands, the second telescopic component including (1) a receiving part having a tube and an arm, and (2) an insertion part including a rod having a first end and a second end, the first end of the rod of the insertion part being slidably disposed in the tube of the receiving part; and, third and fourth bushings for pivotably coupling the second telescopic component to the third and fourth bands, each of the bushings defining a bore and including a slot in communication with the bore, each slot being disposed in a side of its respective bushing, the second end of the rod being pivotably secured in the third bushing with the rod extending through the slot of the third bushing, a first end of the arm associated with the receiving part being pivotably secured in the fourth bushing with the arm extending through the slot of the fourth bushing, at least one of the bushings being removably secured to its respective band by a pin and a locking ring.

13. A method for assembling an apparatus for correcting an overbite in a patient having front premolars in both their upper and lower jaws, the method comprising the steps of:

mounting first and second bands to the front premolars in the patient's upper and lower jaws, respectively;

mounting a first pin on one of the bands and a second pin on the other one of the bands, the first and second pins each having a wall with a circular groove defined therein;

sliding a first locking ring around the wall of the first pin until the locking ring slides into the circular groove of the first pin;

positioning a ball disposed on a rod of an insertion part within a bore defined in a first bushing with the rod extending from a slot defined in a side of the first bushing;

pressing the first bushing onto the first pin such that the wall of the first pin mates with the bore of the first bushing, the bore of the first bushing including a chamfer, the chamfer compressing the first locking ring as the first bushing slides onto the first pin until a groove disposed on an inner surface of the first bushing aligns with the first locking ring whereupon the first locking ring expands to its normal diameter to secure the first bushing to the first pin;

mounting a receiving part having a tube on the rod of the insertion part, the rod being slidably disposed within the tube;

sliding a second locking ring around the wall of the second pin until the second locking ring slides into the circular groove of the second pin;

positioning a ball disposed on the receiving part within a bore defined in a second bushing with the receiving part extending from a slot defined in a side of the second bushing;

pressing the second bushing onto the second pin such that the wall of the second pin mates with the bore of the second bushing, the bore of the second bushing including a chamfer, the chamfer compressing the second locking ring as the second bushing slides onto the second pin until a groove disposed on an inner surface of the second bushing aligns with the second locking ring whereupon the second locking ring expands to its normal diameter to secure the second bushing to the second pin.

* * * * *